(12) United States Patent
Simeth et al.

(10) Patent No.: US 10,114,354 B2
(45) Date of Patent: Oct. 30, 2018

(54) PERSONAL GROOMING APPLIANCE

(71) Applicant: Braun GmbH, Kronberg (DE)

(72) Inventors: Martin Simeth, Koenigstein/Taunus (DE); Leo Faranda, Rodgau (DE); Kervin Heinrich Küchler, Darmstadt (DE); Ralf Schupp, Brechen (DE); Thomas Hoenig, Kronberg (DE)

(73) Assignee: BRAUN GMBH, Kronberg (DE)

( * ) Notice: Subject to any disclaimer, the term of this patent is extended or adjusted under 35 U.S.C. 154(b) by 595 days.

(21) Appl. No.: 14/600,451

(22) Filed: Jan. 20, 2015

(65) Prior Publication Data

US 2015/0205279 A1    Jul. 23, 2015

(30) Foreign Application Priority Data

Jan. 21, 2014 (EP) .................................. 14151940
Nov. 26, 2014 (EP) .................................. 14194876

(51) Int. Cl.
*G05B 19/02* (2006.01)
*A46B 15/00* (2006.01)
(Continued)

(52) U.S. Cl.
CPC .............. *G05B 19/02* (2013.01); *A45D 27/22* (2013.01); *A46B 15/0004* (2013.01);
(Continued)

(58) Field of Classification Search
CPC ...................................................... G05B 19/02
(Continued)

(56) References Cited

U.S. PATENT DOCUMENTS 5,453,644 A    9/1995 Yap et al.
6,798,169 B2   9/2004 Trawinski et al.
(Continued)

FOREIGN PATENT DOCUMENTS

DE         10039472 A1   2/2002
DE   20 2006 016582 U1   1/2007
(Continued)

OTHER PUBLICATIONS

European Search Report dated Jun. 25, 2014.
European Search Report with Written opinion for CM4021; dated Jul. 26, 2016; 15 pages.

*Primary Examiner* — Joseph Chang
(74) *Attorney, Agent, or Firm* — Vladimir Vitenberg

(57) ABSTRACT

A personal grooming appliance has an energy source, an electronic circuit comprising at least one electric load, and a first sensor for providing a first signal indicating a relevant change of a first external condition. The appliance is arranged to stay in a sleep mode in which the electronic circuit consumes at least a reduced average energy amount in comparison to an active mode and to initiate the active mode when the first signal indicating a change of the first external condition is received. The electronic circuit can be arranged to perform a welcome routine in response to a first active mode initialization and a standard routine, different to the welcome routine, in response to receiving the first signal indicating a relevant change in the first external condition after the welcome routine has been performed. The first sensor can be a light sensor, a resistance sensor, a humidity sensor, a gas sensor, or a temperature sensor. A personal grooming appliance unit comprising the personal grooming appliance in combination with a packaging that houses the (Continued)

appliance can include the first sensor that is sensitive to a change of the packaging condition comprising an opening of the packaging.

15 Claims, 2 Drawing Sheets

(51) Int. Cl.
    *A45D 27/22* (2006.01)
    *A61C 17/22* (2006.01)
    *B26B 19/38* (2006.01)
    *B65D 17/28* (2006.01)

(52) U.S. Cl.
    CPC .......... *A61C 17/221* (2013.01); *B26B 19/388* (2013.01); *B65D 17/28* (2018.01); *A46B 2200/1066* (2013.01); *A61C 17/22* (2013.01); *Y10T 307/406* (2015.04)

(58) Field of Classification Search
    USPC ............................................................ 307/31
    See application file for complete search history.

(56) References Cited

U.S. PATENT DOCUMENTS

| | | | |
|---|---|---|---|
| 7,441,336 | B2 | 10/2008 | Hawes et al. |
| 7,443,297 | B1 | 10/2008 | Baranowski et al. |
| 7,628,759 | B2 | 12/2009 | Freund et al. |
| 8,371,896 | B2 | 2/2013 | Baytman et al. |
| 8,604,907 | B2 | 12/2013 | Ludwig et al. |
| 8,943,635 | B2 * | 2/2015 | Heil ................ A61C 17/221 15/22.1 |
| 9,499,323 | B2 | 11/2016 | Simeth |
| 2003/0085687 | A1 | 5/2003 | Trawinski et al. |
| 2005/0131310 | A1 | 6/2005 | Freund et al. |
| 2005/0226446 | A1 | 10/2005 | Luo et al. |
| 2006/0037197 | A1 | 2/2006 | Hawes et al. |
| 2007/0154042 | A1 | 7/2007 | Buckley et al. |
| 2009/0007433 | A1 | 1/2009 | Hawes et al. |
| 2009/0181598 | A1 | 7/2009 | Baytman et al. |
| 2010/0245112 | A1 | 9/2010 | Ludwig et al. |
| 2010/0269276 | A1 | 10/2010 | Faranda et al. |
| 2010/0281636 | A1 | 11/2010 | Ortins et al. |
| 2011/0004325 | A1 | 1/2011 | Ayal |
| 2012/0171657 | A1 | 7/2012 | Ortins et al. |
| 2013/0180062 | A1 | 7/2013 | Huy et al. |
| 2014/0210280 | A1 | 7/2014 | Simeth |

FOREIGN PATENT DOCUMENTS

| | | |
|---|---|---|
| EP | 0 439 725 B | 8/1991 |
| EP | 2 218 559 A1 | 8/2010 |
| EP | 2 550 935 A1 | 1/2013 |
| EP | 2 617 320 A1 | 7/2013 |
| EP | 2 733 570 A2 | 5/2014 |
| JP | 2003310644 | 11/2003 |
| JP | 2009018108 | 1/2009 |
| WO | WO 2003/005873 A1 | 1/2003 |
| WO | WO 2003/035509 A1 | 5/2003 |
| WO | WO 2003/101290 A2 | 12/2003 |
| WO | WO 2003/107507 A1 | 12/2003 |

\* cited by examiner

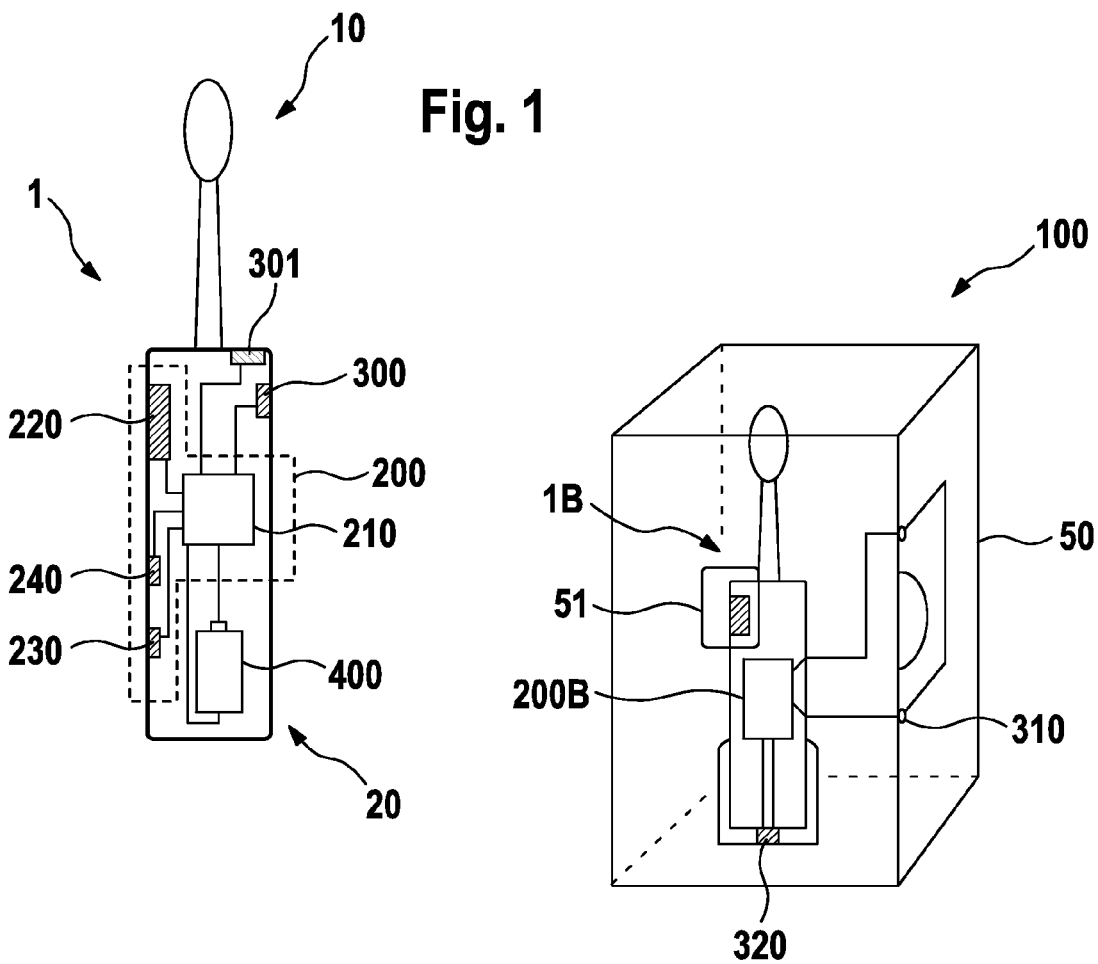
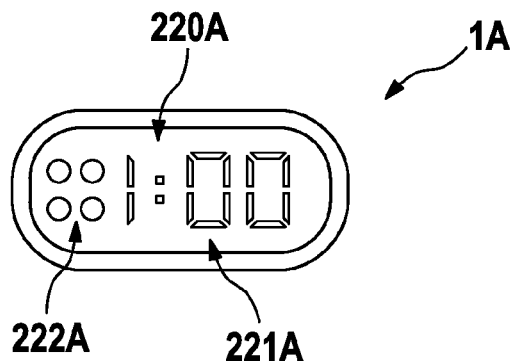

PERSONAL GROOMING APPLIANCE

FIELD OF THE INVENTION

The present invention is concerned with a personal grooming appliance and it is also concerned with a packaged personal grooming appliance unit. In particular, the invention is concerned with a personal grooming appliance having a sleep mode and an active mode.

BACKGROUND OF THE INVENTION

It is known that personal grooming appliances such as, e.g., electric toothbrushes may be packaged in a demonstration mode where a display of the personal grooming appliance is continuously switched on to show potential display content so as to attract the attention of a consumer and to provide information about the capabilities of the personal grooming appliance, while the packaged personal grooming appliance is on a store shelf. Such a demonstration mode consumes energy that typically may be provided by an energy source such as a battery or rechargeable accumulator disposed in a housing of the personal grooming appliance. Thus, when the personal grooming appliance is bought by a consumer and unpacked at the consumer's home, the energy source of the personal grooming appliance may be discharged and the personal grooming appliance may thus not be instantaneously usable after it is unpacked. As an alternative, it is known to package personal grooming appliances in an off mode in which no energy is consumed and usability of the personal grooming appliance is only impacted by any potential energy leakage of the energy source during its shelf life in case that the energy source of the personal grooming appliance was charged prior to packaging. Then, as a consequence, a consumer can, e.g., not be interactively informed by the personal grooming appliance about its capabilities while being packaged.

It is an object of the present disclosure to provide a personal grooming appliance that is improved over the known personal grooming appliances and that is in particular instantaneously usable after being unpacked.

SUMMARY OF THE INVENTION

In accordance with one aspect there is provided a personal grooming appliance, in particular an electric toothbrush or an electric shaver, having an energy source, an electronic circuit comprising at least one electric load, a first sensor for providing a first signal indicating a relevant change of a first external condition, and the personal grooming appliance is arranged to stay in a sleep mode in which the electronic circuit consumes at least a reduced average energy amount in comparison to an active mode and to initiate the active mode when the first signal indicating a change of the first external condition is received, wherein the electronic circuit is arranged to perform a welcome routine in response to a first active mode initialization and a standard routine different to the welcome routine in response to receiving the first signal indicating a relevant change in the first external condition after the welcome routine has been performed.

In accordance with one aspect there is provided a personal grooming appliance, in particular an electric toothbrush or an electric shaver, having an energy source, an electronic circuit comprising at least one electric load, a first sensor for providing a first signal indicating a relevant change of a first external condition, and the personal grooming appliance is arranged to stay in a sleep mode in which the electronic circuit consumes at least a reduced average energy amount in comparison to an active mode and to initiate the active mode when the first signal indicating a change of the first external condition is received, wherein the first sensor is a light sensor, a resistance sensor, a humidity sensor, a gas sensor, or a temperature sensor.

In accordance with one aspect there is provided a packaged personal grooming appliance unit comprising a personal grooming appliance in accordance with any of the preceding claims and a packaging that at least partly houses the personal grooming appliance, wherein the first sensor is sensitive to a change of the packaging condition, in particular to an opening of the packaging.

BRIEF DESCRIPTION OF THE DRAWINGS

The aspects of the present disclosure will be further elucidated by an explanation of general embodiments in accordance with the present disclosure and by a more detailed discussion of example embodiments and by reference to figures. In the figures FIG. 1 is a schematic depiction of a first example embodiment of a personal grooming appliance in accordance with the present disclosure;

FIG. 2 is a schematic depiction of a second example embodiment of a personal grooming appliance in accordance with the present disclosure, where the second example embodiment may be a stand-alone appliance or may be an auxiliary appliance that may be coupled with an appliance as shown in FIG. 1 so that the personal grooming appliance is formed by two separate appliances;

FIG. 3 is a schematic depiction of a packaged personal grooming appliance unit comprising at least one personal grooming appliance and a packaging at least partly housing the personal grooming appliance.

DETAILED DESCRIPTION OF THE INVENTION

Figure 4:
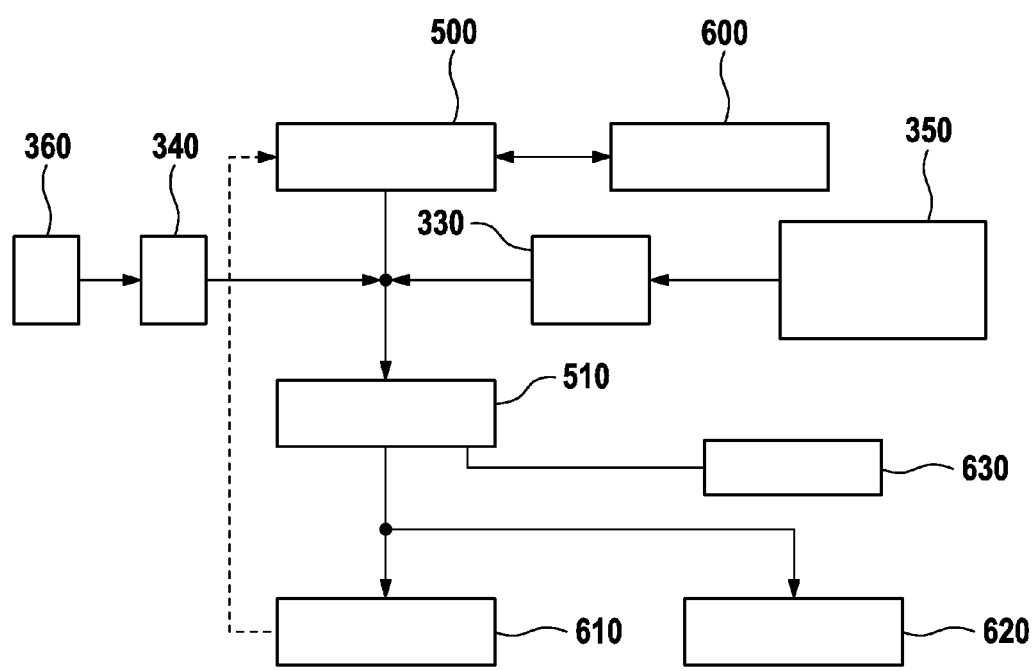
FIG. 4 is a flow chart indicating an example embodiment of operating a personal grooming appliance in accordance with the present disclosure.

In accordance with the present disclosure, a personal grooming appliance (e.g. an oral hygiene device such as an electric toothbrush, an oral irrigator, a flossing device, a gum massaging device etc., an electric shaver, an electric epilator, a massaging device, a skin treatment device etc.) is in a sleep mode in which an electronic circuitry having at least one electric load is consuming at least less energy than in an active mode and the personal grooming appliance has at least a first sensor for detecting a first external condition, where the personal grooming appliance is arranged to initiate the active mode upon a first signal from the first sensor indicating that the first external condition has changed in a relevant manner (i.e. a threshold value was crossed). At least one routine may be automatically started after initialization of the active mode, e.g. the active mode may include a welcome routine, a standard routine, a wake-up routine, or a shelf routine. The first sensor may in particular be one from the group consisting of light sensors, electromagnetic field sensors such as Hall sensors, capacitance sensors, resistance sensors, inductive sensors, humidity sensors, gas sensors, and temperature sensors. In some embodiments, the personal grooming appliance starts a welcome routine if the first signal is received for the first time and a standard routine if the first signal is received for second or further time. Optionally, the personal grooming appliance comprises at least a second sensor for monitoring a second condition and for providing a second signal in case the second signal has changed in a relevant manner. The second sensor may then be chosen from the same group of sensors, but the second sensor may alternatively also be a sensor that detects an internal condition of the personal grooming device, e.g. the second sensor may alternatively be realized as a position or acceleration sensor, as a pressure sensor or as a vibration sensor. Thus, such a second sensor could then be arranged to detect a second condition that might be an external condition or an internal condition. In some embodiments, the personal grooming appliance comprises at least one of a display, a light emission diode, or an audio unit as load. In the active mode (e.g. as part of one of the mentioned routines), the electronic circuit may then activate the display for a preset time and/or may present preset textual and/or graphic information on the display, may activate the light emission element for a preset period and/or may activate the audio unit for a preset time period to reproduce preset audio signal/content.

The provision of a sleep mode at least provides a slower discharge of the energy source in comparison to a personal grooming appliance always being in an active mode. In some embodiments, the electronic circuit may be completely switched off in the sleep mode and the first signal (e.g. provided by a light sensor) may comprise enough energy content to activate the electronic circuit. Alternatively, the electronic circuit may have switched off main energy consuming parts such as a DC-DC converter and may in the sleep mode only monitor the first sensor, which can be realized with very low energy consumption.

It shall be noted that a change of an "external condition" in accordance with the present disclosure means a change of a condition that is effectively independent from the personal grooming appliance (i.e. the status of the personal grooming appliance does not need to be changed to change the external condition). Such a change may be a change in the ambient light condition (which may happen due to switching on/off an ambient light source or by unpacking the personal grooming appliance). The change of the external condition may also be constituted by an approximation of an object or subject (e.g. a consumer's hand), by a change of the ambient temperature or humidity, by change of the resistance of an external resistor to which the first sensor is connected etc. For sake of completeness, a change of an "external condition" is not constituted by a movement of the personal grooming appliance itself, by a force being applied at the personal grooming appliance or the like, which are considered as "internal conditions" as they relate to changes happening with the personal grooming appliance.

The following provides explanations of the modes and routines that are discussed in the present disclosure. The precise content of the routines may be stored in a respective storage element of the electronic circuit.

"Sleep mode": A sleep mode is a mode of the personal grooming appliance in which it at least consumes in average less energy from an energy source than in an "active mode" (see below), in particular the personal grooming appliance may in the sleep mode not consume any energy at all.

The personal grooming appliance is arranged to automatically initiate an "active mode" when a relevant change of at least a first external condition is detected.

"Active mode": An active mode is a mode in which the personal grooming appliance consumes in average more energy than in the sleep mode. In particular, the active mode includes monitoring the switches of the personal grooming appliance by the electronic circuit. The electronic circuit may be preprogrammed to perform certain activities and such activities may include any of the below routines. In some embodiments, the personal grooming appliance is further arranged to initiate an active mode on a random or pseudo-random basis as long as it is in the sleep mode and to fall back into the sleep mode after a certain (preset) period. In particular, the personal grooming appliance may then activate a "shelf routine" (see below).

"Welcome routine": A welcome routine is a routine that shall be started when a relevant change in at least the first external condition is detected for the first time, e.g. when a consumer unpacks the personal grooming appliance at home, and the welcome routine may be intended to establish a personal bond between the consumer and the personal grooming appliance. The welcome routine may include one or more input invitations during which the owner of the personal grooming appliance may, e.g., be asked to enter his or her name in order to personalize the personal grooming appliance, while this shall not exclude that the welcome routine comprises only lighting up of one or more light emission elements and/or displaying particular information about the personal grooming appliance without any interactivity.

"Standard routine": A standard routine is a pre-programmed or customizable sequence of activities the personal grooming appliance performs when e.g. a relevant change of the first external condition is indicated for a second or further time or a relevant change in a second condition is detected. The standard routine may comprise a short activation of at least one light emission element for a preset period so that e.g. the user is informed that the personal grooming appliance has detected that it has been gripped or a consumer is about to grip it (where the relevant change of the first external or second condition is related to a relevant change in the capacitive external condition indicating a close proximity of, e.g., a hand of a consumer).

"Wake-up routine": A wake-up routine is a pre-programmed sequence of activities, e.g. of information being displayed on a display of the personal grooming appliance, that the manufacturer may have considered as useful for attracting consumers, while the personal grooming appliance is placed on a shelf at a point of sales under the condition that a relevant change in a second condition indicates that a consumer is close to the personal grooming appliance, e.g. because the second sensor being realized as a capacitance sensor indicates that the personal grooming appliance is being held by a consumer. A wake-up routine may include an input invitation during which the electronic circuit waits for a consumer to push a button or the like in order to receive more information etc. Without any input, the wake-up routine may be stopped after a pre-set time period after which the sleep mode is reentered.

"Shelf routine": a shelf routine may either be a pre-programmed sequence of activities, e.g. of information being displayed on a display of the personal grooming appliance, that the manufacturer may have considered as useful for attracting consumers while the personal grooming appliance is placed on a shelf at a point of sales or it may be identical to the above described wake-up routine. The shelf routine is intended to be started for a determined time period on a random or pseudo-random basis (where in this disclosure, "random" or "randomly" shall include "pseudo-random" or "pseudo-randomly") while the personal grooming appliance is in the sleep mode. After the determined time period, the personal grooming appliance will automatically be set back into the sleep mode.

FIG. 1 is a schematic depiction of a first example embodiment of a personal grooming appliance 1 in accordance with the present disclosure. The personal grooming appliance may be realized as an electric toothbrush comprising a head 10 (here: a brush head) and a handle 20. In other embodiments, the personal grooming appliance may be realized as an electric epilator, an electric shaver, a hair dryer or a gum massaging device.

The personal grooming appliance 1 comprises an electronic circuit 200 having at least one electric load 220, at least a first sensor 300 for providing a first signal indicating a relevant change of a first external condition, and an energy source 400. The first sensor 300 may provide the first signal, when a respective sensor value (e.g. reflecting the ambient light intensity measured with the first sensor realized as a light sensor) crosses a predetermined threshold value, thus indicating the relevant change. The first sensor 300 may be chosen as a sensor from the group as listed before. The first sensor 300 may thus be sensitive to a change in the ambient light condition if it is realized as a light sensor (e.g. comprising a photodiode). If realized as a capacitive sensor, the first sensor 300 may be sensitive to changes in its environment, i.e. may detect the presence of the hand of a user in its close proximity. The electronic circuit 200 may in particular comprise a control circuit 210 for controlling, e.g., a display or light emitting elements or an audio unit for reproduction of audible signals. In some embodiments, the electronic circuit 200 comprises two electric loads 220, 230 (e.g. a display 220 and at least one light emitting element 230) or even more electric loads 220, 230, 240 (including a further light emission element 240). In some embodiments, the electric load 220 may be one from the group consisting of light emitting elements, information displaying elements, and audio and/or video signal reproducing elements (e.g. a loudspeaker). In embodiments with two or more electric loads, each of the electric loads may be one from the group previously listed. Optionally, the personal grooming appliance 1 comprises at least a second sensor 301 for providing a second signal indicating a relevant change of a second condition different to the first external condition. The relevant change may again be determined by a sensor value crossing a predetermined threshold value. The electronic circuit 200 may be coupled to the energy source 400 and to the first sensor 300 (optionally to a second sensor 301).

The electronic circuit 200 is arranged to switch the personal grooming appliance from a sleep mode into an active mode when the first sensor 300 provides a first signal indicating a relevant change in the first external condition. In some embodiment, in the active mode a welcome routine is started in case that the electronic circuit 200 detects that it was activated for the first time and a standard routine is started in case that the welcome routine had already been activated before (i.e. the active mode is initiated for a second or further time). In some embodiments, the electronic circuit 200 is arranged to switch off the first sensor 300 after the first active mode initialization and the personal grooming appliance 1 may from this point in time on only be activated by the user via an on/off switch button.

FIG. 2 is a schematic depiction of a personal grooming appliance 1A realized as a small display device having a display 220A that may have a first display area 221A for e.g. displaying a time information and a second display area 222A for displaying additional information. In some embodiments, the personal grooming appliance in accordance with the present disclosure may comprise two separate units, e.g. a toothbrush and a display unit that may be wirelessly connected with each other so that displaying of information on the display unit can be controlled by the toothbrush.

FIG. 3 is a schematic depiction of a packaged personal grooming appliance unit 100 in accordance with the present disclosure. The packaged personal grooming appliance unit 100 comprises a personal grooming appliance 1B and a packaging 50 that at least partly houses the personal grooming appliance 1B. The packaging may comprise a transparent window 51 through which at least a part of the personal grooming appliance 1B is visible. The visible part of the personal grooming appliance 1B may comprise at least one light emitting element and/or a display. The first sensor 310 is here arranged to sense a change in the packaging condition, e.g. the first sensor 310 may be a light sensor arranged at a portion of the personal grooming appliance 1B that is covered by the packaging 50, so that ambient light impinges onto the first sensor 310 once the packaging 50 is opened.

At least one of the first or optional second sensors 310, 320 may be connected with an element outside of the personal grooming appliance 1B, e.g. the first sensor 310 may be coupled with a thin wire crossing a part of the packaging 50 that needs to be separated when opening the packaging 50 so that opening the packaging 50 (i.e. changing the packaging condition) could be sensed (e.g. by breaking the conductive thin wire coupled with a resistance sensor realizing the first sensor 310—the thin wire thus represents a seal element). Example embodiments are discussed in the following. In the shown embodiment, an optional second sensor 320 may be realized as a capacitance sensor that is able to detect when the personal grooming appliance is gripped.

EXAMPLE 1

In the first example, the packaged personal grooming appliance comprises a light sensor (e.g. realized as a photodiode) that in the packaged state does not provide a first signal due to the lack of sufficient light impinging onto the sensor. The electronic circuit thus stays in a sleep mode as long as it is packaged. As the photodiode may energize itself from light impinging onto it, there is not even the need to spend energy for keeping the first sensor in a sensing state. Thus, besides any leakage issues, the energy source (e.g. a rechargeable accumulator such as a Li-ion accumulator) is not discharged and the personal grooming appliance will be instantaneously useable when it is unpacked because the accumulator is essentially fully charged.

In a modified example 1, the electronic circuit comprises a clocking circuit that periodically (i.e. after a preset time period) or randomly activates the electronic circuit for preset time intervals. When the electronic circuit is activated by the clocking circuit, it is arranged to start a shelf routine in which the personal grooming appliance e.g. displays information on a display (representing an electric load) for a preset time period. After the preset time period, the electronic circuit deactivates the electronic circuit and sets it to sleep mode again.

When the personal grooming appliance is unpacked (the packaging condition is changed), light will impinge onto the light sensor and the light sensor will thus provide a first signal indicating a relevant change in the first external condition, i.e. the external light condition. The electronic circuit will, as a response to receiving the first signal for a first time, initiate an active mode and start a welcome routine. Thereafter, the electronic circuit may start a standard routine, if the first signal is received again or the electronic circuit may switch off the first sensor after the welcome routine had been started.

EXAMPLE 2

In the second example, the first sensor is realized as a resistance sensor. The resistance sensor may be coupled with a conducting wire that crosses over a part of the packaging that needs to be opened to unpack the personal grooming appliance, upon which opening the wire would be torn apart, which would trigger the first sensor to provide a first signal (thus, the thin wire represents a seal element). Breakage of the conducting wire (i.e. opening of the packaging) would then trigger an active mode and the start of a welcome routine. A second sensor, realized as a capacitance sensor, may be arranged to detect the proximity of a consumer. Upon relevant change of the capacitance value measured by the second sensor, the second sensor provides a second signal, and the personal grooming appliance is set to the active mode in which a wake-up routine is initiated. After the personal grooming appliance is unpacked and the first signal had been received, the electronic circuit may then be arranged to initiate a standard routine upon reception of the second signal instead of the wake-up routine. The standard routine may include lighting up all light emitting elements for a preset period, thereby reassuring the user that the personal grooming appliance has noted that the user has gripped it or is about to grip it.

FIG. 4 is a flow chart diagram schematically depicting an example embodiment of operating a personal grooming appliance in accordance with the present disclosure. In a first state 500, the personal grooming appliance is in a sleep mode in which the electronic circuit in average consumes less energy than in an active state (e.g. an electric load such as a display unit is switched off). Optionally, the personal grooming appliance may be arranged to periodically or randomly switch on an active mode in which a shelf routine 600 is started in which e.g. a display unit will display information (e.g. textual and/or graphical information may be displayed). The personal grooming appliance is then arranged to automatically switch off the shelf routine after a preset time period and to restore the sleep mode 500. The shelf routine 600 may attract consumers by displaying information while the personal grooming appliance is on a shelf in a shop, but as the shelf mode may only be switched on, e.g., for a fifth or tenth or even lower fraction of the overall shelf life of the personal grooming appliance, less energy is consumed in comparison to an uninterrupted shelf routine.

In the event that a change of a first external condition 350 triggers a first sensor 330 to provide a first signal, the personal grooming appliance switches into an active mode 510. Optionally, the personal grooming appliance switches into the active mode 510 also on reception of a second signal from a second sensor 340 indicating a change of a second condition 360. The personal grooming appliance will then activate a welcome routine 610 in case that the first signal was received for the first time (optionally, also in case the second signal was received for the first time and no first signal was received so far). In case that the welcome routine 610 had already been activated before, the personal grooming appliance may optionally activate a standard routine 620 different to the welcome routine 610. After initiation of the welcome routine 610, the personal grooming appliance may stay in the active mode 510 or, alternatively, may switch back into the sleep mode 500. In case of an optional shelf mode 600, the periodic or random shelf mode activation may be switched off as it is then assumed that the personal grooming appliance is now in a user's home. After having activated the welcome mode 610, the personal grooming appliance may switch into the active mode only upon reception of a second signal from the second sensor 340 indicating a change in the second condition. E.g. the first sensor 350 may be realized as a light sensor that activates the active mode in which the welcome routine 610 is initiated (the light sensor would, e.g., trigger the first signal when the personal grooming appliance is unpacked and the light sensor is exposed to ambient light) and the second sensor may be realized as a proximity sensor (e.g. a capacitive sensor) for detecting that a user has gripped or is about to grip the personal grooming appliance. Alternatively, in embodiments with a second sensor, the second signal may trigger a wake-up routine 630 as long as the first signal has not been received. The second signal received prior to the first signal in the before discussed embodiment would then indicate that a consumer has taken the package with the personal grooming appliance off a shelf. The wake-up routine could then include displaying of information on a display unit so that the consumer is informed about the product.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A packaged personal grooming appliance unit, in combination with a packaging that at least partly houses the personal grooming appliance, comprising a personal grooming appliance including
   an energy source;
   an electronic circuit comprising at least one electric load;
   a first sensor for providing a first signal indicating a relevant change of a first external condition;
   wherein the personal grooming appliance is arranged to stay in a sleep mode in which the electronic circuit consumes at least a reduced average energy amount in comparison to an active mode and to initiate the active mode when the first signal indicating a change of the first external condition is received;

wherein the electronic circuit is arranged to perform a welcome routine in response to a first active mode initialization and a standard routine, different from the welcome routine, in response to receiving the first signal indicating a relevant change in the first external condition after the welcome routine has been performed, and wherein the first sensor is sensitive to a change of the packaging condition comprising at least an opening of the packaging.

2. The personal grooming appliance in accordance with claim 1, wherein the first sensor is chosen from the group consisting of light sensors, electromagnetic field sensors, Hall sensors, capacitance sensors, resistance sensors, inductive sensors, humidity sensors, gas sensors, temperature sensors, and any combination thereof.

3. A packaged personal grooming appliance unit, in combination with a packaging that at least partly houses the personal grooming appliance, comprising a personal grooming appliance including an energy source;

an electronic circuit comprising at least one electric load;

a first sensor for providing a first signal indicating a relevant change of a first external condition;

wherein the personal grooming appliance is arranged to stay in a sleep mode in which the electronic circuit consumes at least a reduced average energy amount in comparison to an active mode and to initiate the active mode when the first signal indicating a change of the first external condition is received;

wherein the first sensor is selected from the group consisting of a light sensor, a resistance sensor, a humidity sensor, a gas sensor, a temperature sensor, and any combination thereof, and wherein the first sensor is sensitive to a change of the packaging condition comprising at least an opening of the packaging.

4. The personal grooming appliance in accordance with claim 1, wherein the first signal has an energy content allowing activating the electronic circuit for initiating the active mode.

5. The personal grooming appliance in accordance with claim 1, further comprising a display as the electric load, wherein the welcome routine at least includes displaying preset information on the display.

6. The personal grooming appliance in accordance with claim 1, further comprising a light emission element as the electric load, wherein the welcome routine at least includes switching-on of the light emission element for a preset period.

7. The personal grooming appliance in accordance with claim 1, further comprising an audio unit for producing audible signals, wherein the welcome routine at least includes producing at least one preset audio signal.

8. The personal grooming appliance in accordance with claim 1, further comprising at least a second sensor for providing a second signal indicating a relevant change of a second condition different from the first external condition.

9. The personal grooming appliance in accordance with claim 8, wherein the electronic circuit is arranged to initiate the active mode also in response to receiving the second signal.

10. The personal grooming appliance in accordance with claim 8, wherein the electronic circuit is arranged to perform a welcome routine in response to receiving the first signal and to perform a wake-up routine, different from the welcome routine, in response to receiving the second signal.

11. The personal grooming appliance in accordance with claim 1, wherein the electronic circuit is arranged to periodically or randomly perform a shelf routine, different from the welcome routine, as long as no first signal has been received.

12. The packaged personal grooming appliance unit in accordance with claim 1, wherein the package covers at least the first sensor.

13. The packaged personal grooming appliance unit of claim 1, wherein the first sensor comprises a light sensor and wherein the package efficiently seals the first sensor from ambient light.

14. The packaged personal grooming appliance unit in accordance with claim 1, wherein the package comprises a seal element that is structured and configured to be broken either when the package is opened or when the personal grooming appliance is removed from the package and wherein the first sensor is arranged to detect the breakage of the seal element as a change of the first external condition.

15. The personal grooming appliance of claim 1, wherein the personal grooming appliance is selected from the group consisting of an electric toothbrush and an electric shaver.

* * * * *